(12) United States Patent
Jobin et al.

(10) Patent No.: US 7,437,957 B2
(45) Date of Patent: Oct. 21, 2008

(54) POROUS MEDIUM TENSIOMETER

(75) Inventors: Philippe Jobin, Québec (CA); Jean Caron, Saint-Romuald (CA); Sébastien Descoteaux, Saint-Jean-Chrysostome (CA); Jocelyn Boudreau, Lévis (CA)

(73) Assignee: Hortau Inc., Quebec ( * ) Notice: Subject to any disclaimer, the term of this patent is extended or adjusted under 35 U.S.C. 154(b) by 131 days.

(21) Appl. No.: 11/503,909

(22) Filed: Aug. 15, 2006

(65) Prior Publication Data
US 2008/0041170 A1     Feb. 21, 2008

(51) Int. Cl.
*G01L 1/02*     (2006.01)

(52) U.S. Cl. .................... 73/862.581; 73/73; 73/74; 73/826

(58) Field of Classification Search ......... 73/73, 73/74, 826, 862.581
See application file for complete search history.

(56) References Cited

U.S. PATENT DOCUMENTS

| | | | |
|---|---|---|---|
| 2,863,698 A | 12/1958 | Richards | |
| 2,878,671 A | 3/1959 | Prosser et al. | |
| 3,045,477 A | 7/1962 | Matson | |
| 3,049,914 A | 8/1962 | Richards | |
| 3,806,851 A | 4/1974 | McCormick | |
| 3,898,872 A | 8/1975 | Skaling et al. | |
| 4,332,172 A | 6/1982 | Torstensson | |
| 4,548,225 A | 10/1985 | Busalacchi | |
| 4,845,978 A * | 7/1989 | Whitford ................. | 73/73 |
| 4,922,945 A * | 5/1990 | Browne ................. | 137/78.3 |
| 5,000,051 A * | 3/1991 | Bredemeier ............ | 73/863.23 |
| 5,156,179 A | 10/1992 | Peterson et al. | |
| 5,179,347 A | 1/1993 | Hawkins | |
| 5,644,947 A | 7/1997 | Hubbell et al. | |
| 5,758,538 A | 6/1998 | Hubbell et al. | |
| 5,915,476 A | 6/1999 | Hubbell et al. | |
| 5,941,121 A | 8/1999 | Faybishenko | |

(Continued)

FOREIGN PATENT DOCUMENTS

EP     1396722 A1     3/2004

OTHER PUBLICATIONS

Thalheimer, M., Tensiometer modification for diminishing errors due to the fluctuating inner water column, Soil Sci. Am. J. 67:737-739 (2003).

(Continued)

*Primary Examiner*—Edward Lefkowitz
*Assistant Examiner*—Freddie Kirkland, III
(74) *Attorney, Agent, or Firm*—Ogilvy Renault, LLP

(57) ABSTRACT

A porous medium tensiometer has a filling mechanism which allows to fill a fluid chamber and simultaneously withdraw gas contained in the fluid chamber. A self-priming tensiometer includes a porous material tip having a first section surrounded by a fluid-impermeable membrane, a second section, a threshold suction range and pores, the pores auto-filling with liquid when in fluid communication with a porous medium having a liquid potential being at least equal, in absolute value, to the threshold suction range, the liquid contained in the pores having a liquid pressure representative of the liquid potential; a one-way fluid control device in fluid communication with the porous material tip and allowing fluid contained in pores of the porous material to exit therethrough when the porous material tip auto-fills with liquid; and a pressure transducer in liquid communication with the porous material tip.

21 Claims, 12 Drawing Sheets

U.S. PATENT DOCUMENTS

| | | | |
|---|---|---|---|
| 6,308,563 | B1 | 10/2001 | Hubbell et al. |
| 6,405,588 | B1 | 6/2002 | Hubbell et al. |
| 6,532,803 | B2 | 3/2003 | Hutchinson et al. |
| 6,539,780 | B2 | 4/2003 | Hubbell et al. |
| 6,752,007 | B1 | 6/2004 | Hubbell et al. |
| 6,976,386 | B1 | 12/2005 | Grover et al. |
| 7,042,234 | B2 | 5/2006 | Buss |
| 7,311,011 | B2 * | 12/2007 | Clark et al. .............. 73/864.74 |
| 2005/0120813 | A1 * | 6/2005 | Clark et al. ................ 73/866.5 |

OTHER PUBLICATIONS

Hubbell, J.M., & J.B. Sisson, Comments on "Tensiometer modification for diminishing errors due to the fluctuating inner water column", Soil Sci. Soc. Am. J., 68:709-710 (2004).

Gee, G.W., amd M.D. Campbell, A Wick tensiometer to measure low tensions in coarse soils, Soil Sci. Soc. Am. J., 54:1498-1500 (1990).

Ghodrati, M., F. Ernst, and W.A. Jury, Automated spray system for application of sollutes to small field plots, Soil Sci. Soc. Am. J. 54:287-290 (1990).

Atteia, O., and J.P. Dubois, Automatic acquisition of data from tensiometers with mercury manometers, Soil Sci. Soc. Am. J. 57:689-690 (1993).

Williams, T.H.L., An Automatic scanning and recording tensiometer system, Journal of Hydrology 39:175-183 (1978).

Hubbell, J.M., and J.B. Sisson, Portable tensiometer use in deep boreholes, Soil Science vol. 161, No. 6, 376-381 (1996).

Hubbell, J.M., and J.B. Sisson, Advanced tensiometer for shallow or deep soil water potential measurements, Soil Science vol. 163, No. 4, 271-277 (1998).

Strebel, O., Renger, & Giesel, Soil-suction measurements for evaluation of vertical water flow at greater depths with a pressure transducer tensiometer, J. Hydrol. 18:367-370.

T5—Miniature Pressure Transducer Tensiometer, User Manual—Version 1.8, available on Website www.ums-muc.de,UMS GmbH, Munich, 2005.

* cited by examiner

POROUS MEDIUM TENSIOMETER

FIELD OF THE INVENTION

The invention relates to tensiometers for measuring soil water potential in porous media and, more particularly, it relates to a liquid filling design for tensiometers and to self-priming tensiometers.

DESCRIPTION OF THE PRIOR ART

Tensiometers for monitoring matric water potential $\Psi_m$ (or soil moisture tension, in soil are known. Matric water potential is an indirect measure of soil water content. Tensiometers are used in irrigation scheduling to help farmers and other irrigation managers to determine when to water. In conjunction with a water retention curve, tensiometers can be used to determine how much to water. Tensiometers can also be used in the scientific study of soils and plants.

To reduce farmer's workload such as the tensiometer maintenance and the reading adjustements in accordance with the water level in the tensiometer, there is a need for tensiometers which are easier to use.

BRIEF SUMMARY OF THE INVENTION

It is therefore an aim of the present invention to address the above mentioned issues.

According to an aspect, there is provided a porous medium tensiometer. The porous medium tensiometer comprises: a housing defining a fluid chamber therein and having a fluid channel extending therethrough, the fluid channel having a first port in fluid communication with the fluid chamber and a second port in fluid communication with the atmosphere, the housing being adapted to be at least partially inserted in a porous medium; and a liquid injector insertable in the fluid channel through the second port of the fluid channel for injecting a liquid into the fluid chamber through the first port of the fluid channel and simultaneously ejecting gas contained in the fluid chamber in the atmosphere through the second port.

According to another aspect, there is provided a porous medium tensiometer comprising: a housing defining a fluid chamber therein and having an inner plug provided above the fluid chamber, the inner plug having a fluid channel and a gas exit channel extending therethrough, the fluid channel having a first port in fluid communication with the fluid chamber and a second port in fluid communication with the atmosphere, the gas exit channel having a first port in fluid communication with the fluid chamber and a second port in fluid communication with the fluid channel and merging therewith, the second port of the gas exit channel remaining unobstructed when filling the fluid chamber with liquid through the fluid channel and allowing gas contained in the fluid chamber to exit therethrough.

According to another aspect, there is provided a self-priming tensiometer omprising: a porous material tip having a first section surrounded by a fluid-impermeable membrane, a second section, a threshold suction range and pores, the pores auto-filling with liquid, through the second section, when in fluid communication with a porous medium having a liquid potential being at least equal, in absolute value, to the threshold suction range, the liquid contained in the pores having a liquid pressure representative of the liquid potential; a one-way fluid control device in fluid communication with the porous material tip, through the first section, and allowing fluid contained in pores of the porous material to exit therethrough when the porous material tip auto-fills with liquid; and a pressure transducer in liquid communication with the porous material tip and measuring the liquid pressure therein when the pores are filled with liquid.

According to a further aspect, there is provided a self-priming tensiometer insertable in a porous medium, the self-priming tensiometer comprising: a housing; a porous material tip mounted to the housing and having pores and a threshold suction range, the pores being in fluid communication with the porous medium when inserted therein and auto-filling with liquid when the porous medium has a liquid potential at least equal, in absolute value, to the threshold suction range; a pressure transducer in fluid communication with the porous material tip; and a gas exit valve extending between the housing and the porous material tip and movable between a closed position preventing fluid communication between the porous material tip and the housing and an open position allowing gas contained in the pores of the porous material tip to exit therethrough.

According to still another general aspect, there is provided a porous medium tensiometer comprising: a housing defining a fluid chamber therein, having a fluid channel and a gas exit channel extending therethrough, the fluid channel having a first fluid port in fluid communication with the fluid chamber and a second fluid port in fluid communication with the atmosphere, and the gas exit channel having a first gas port in fluid communication with the fluid chamber and a second gas port in fluid communication with the fluid channel, the gas exit channel merging with the fluid channel at the second gas port and being in fluid communication with the atmosphere Through the second fluid port, the housing being adapted to be at least partially inserted in a porous medium; and a liquid injector insertable in the fluid channel though the second fluid port of the fluid channel for the injection of a liquid into the fluid chamber though the first fluid port of the fluid channel and simultaneously ejecting gas contained in the fluid chamber in the atmosphere through the gas exit channel and the second fluid port.

According to a further general aspect, there is provided a porous medium tensiometer comprising: a housing defining a fluid chamber therein and having an inner plug provided above the fluid chamber, the inner plug having a fluid channel and a gas exit channel extending therethrough, the fluid channel having a first fluid port in fluid communication with the fluid chamber and a second fluid port in fluid communication with the atmosphere, the gas exit channel having a first gas port in fluid communication with the fluid chamber and a second gas port in fluid communication with the fluid channel and merging therewith at the second gas port, the second gas port of the gas exit channel remaining unobstructed when filling the fluid chamber with liquid though the fluid channel and allowing gas contained in the fluid chamber to exit therethrough.

In this specification. The term "porous medium" is intended to mean the soil of a field in agriculture, or the soil of pots for growing plants in a greenhouse or in a nursery, and any porous medium which fills with liquid. It can also be called a substrate, a mixture, a medium, or a soilless medium.

BRIEF DESCRIPTION OF THE DRAWINGS

FIG. 9a is a detailed view, enlarged, of a section of the tensiometer apparatus shown in FIG. 9;

It will be noted that throughout the appended drawings, like features are identified by like reference numerals.

DETAILED DESCRIPTION

Figure 1:
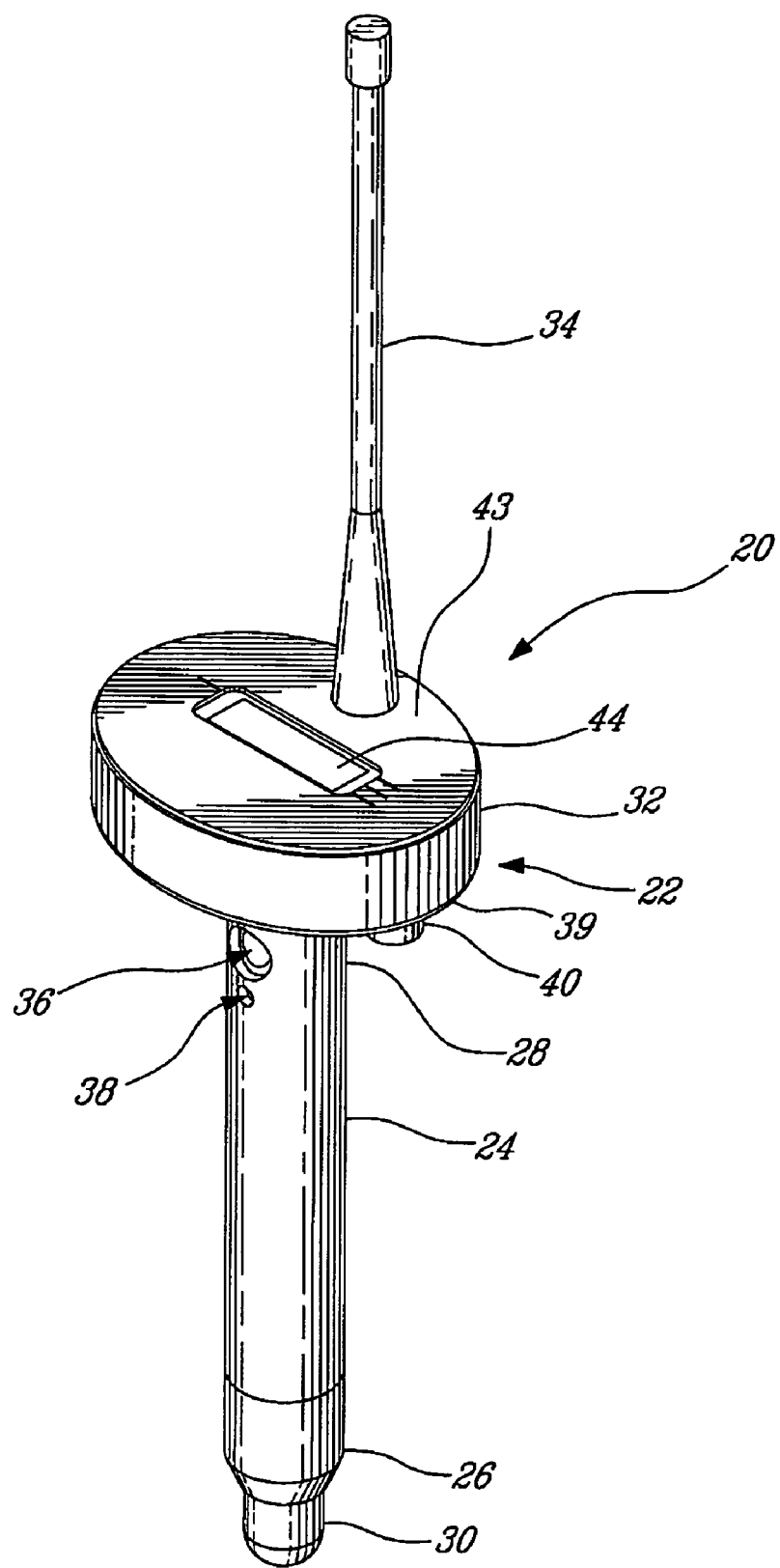
FIG. 1 is a perspective view of a tensiometer apparatus in accordance with an embodiment of the invention.

Referring to the drawings and, more particularly, to FIG. 1, it will be seen a tensiometer apparatus 20 (or water potential sensor) in accordance with an embodiment. The tensiometer 20 is designed to monitor matrix water potential in a porous medium such as, for instance, earthen soil or greenhouse soil.

The tensiometer apparatus 20 has a body 22 which includes a tubular housing 24 with a lower end 26 and an upper end 28, a porous material tip 30, a head 32, and an antenna 34. The porous material tip 30 is mounted to the lower end 26 of the tubular housing 24. The porous material tip 30 has a first section which extends in the tubular housing 24 and a second section which is in direct contact with the porous medium when inserted therein, as will be described in more details below.

The head 32 of the tensiometer 20 is mounted to the upper end 28 of the tubular housing 24. The antenna 34 is mounted to the head 32 of the tensiometer apparatus 20, the purpose of which will be described below. The head 32 and the antenna 34 extend above the porous medium when the tensiometer 20 is inserted therein.

The tubular housing 24 has a liquid inlet aperture 36 (or fluid aperture) and a gas inlet aperture 38 which extends therethrough. These apertures 36 and 38 are proximate to the upper end 28 of the tubular housing 24. In the embodiment shown, the gas inlet aperture 38 is located below the liquid inlet aperture 36 and is longitudinally in line therewith. However, in an alternative embodiment, these apertures 36 and 38 could be positioned differently. The liquid inlet aperture 36 and the gas inlet aperture 38 extend above the porous medium when the tensiometer 20 is inserted therein.

The lower face 39 of the head 32 has two connectors 40, 42 (FIGS. 2-4) extending downwardly therefrom. The purpose of these connectors 40, 42 will be described in more details below.

The upper face 43 of the head 32 includes an electronic dial 44. The electronic dial 44 can display, amongst others, the matrix water potential measured by the tensiometer 20.

Figure 2:
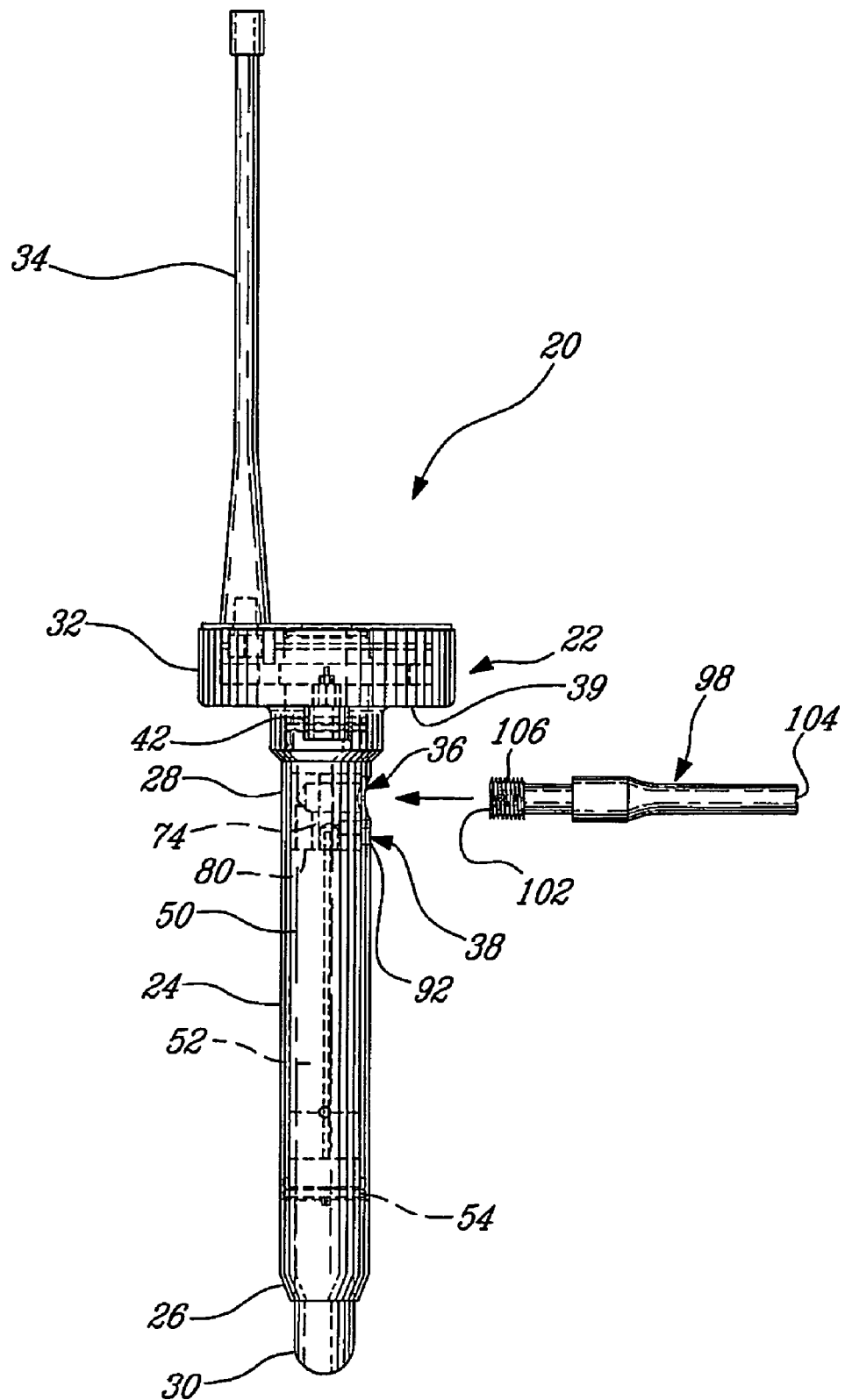
FIG. 2 is side elevation view of the tensiometer apparatus shown in FIG. 1, showing, in dashed lines, internal components of the tensiometer apparatus.
Figure 3:
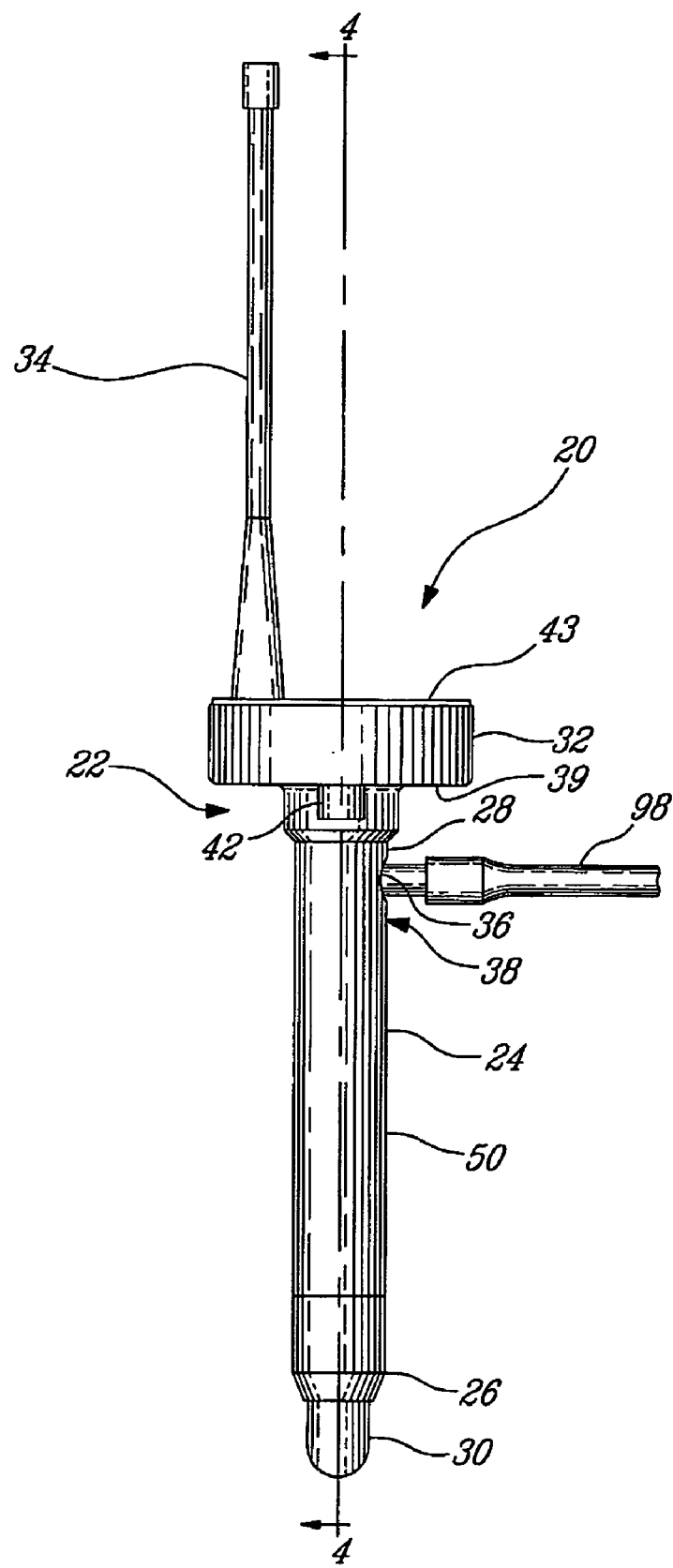
FIG. 3 is side elevation view of the tensiometer apparatus shown in FIG. 1.
Figure 4:
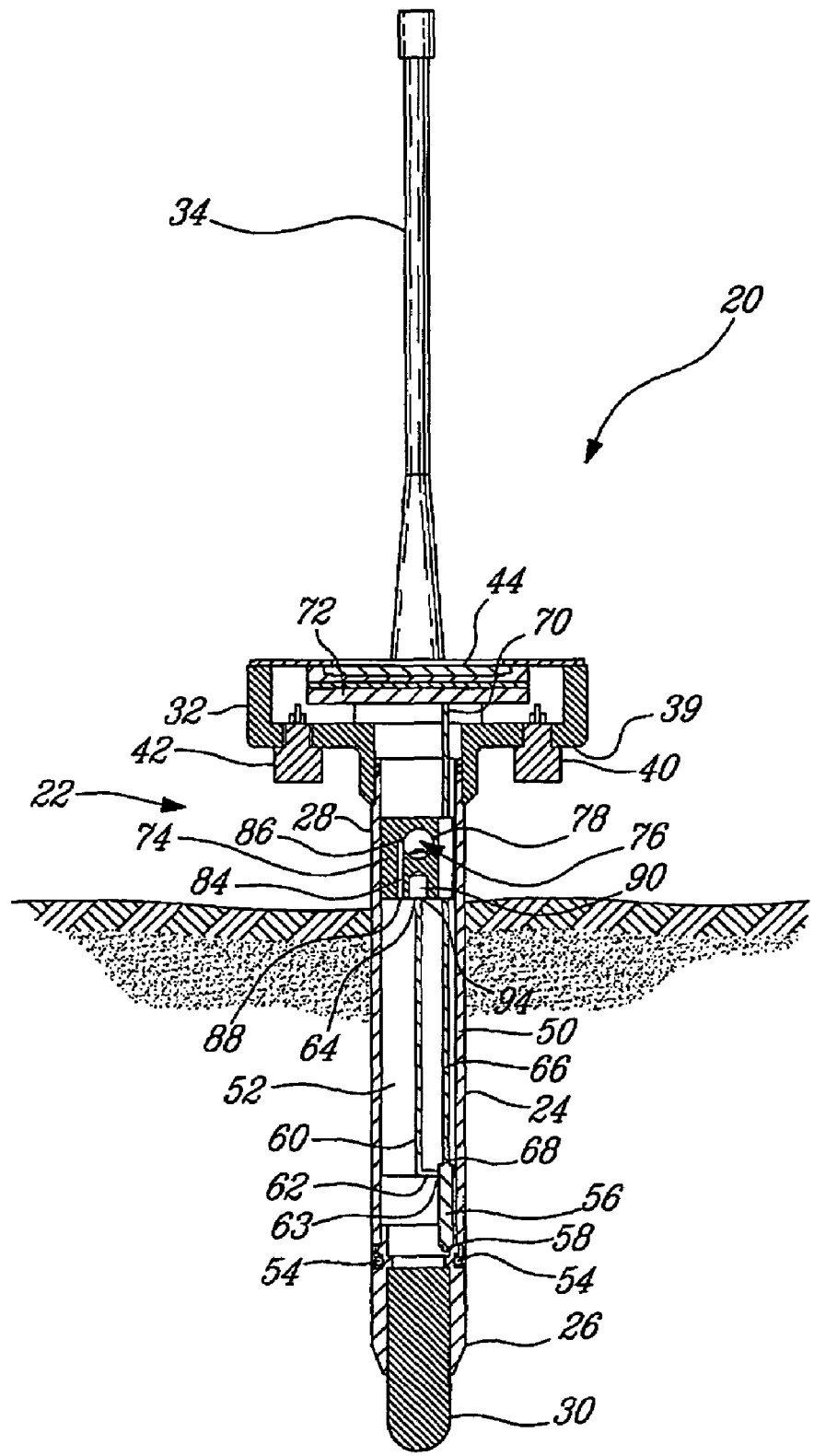
FIG. 4 is a sectional view taken along lines 44 of FIG. 3, wherein the tensiometer apparatus is inserted in a porous medium.

Referring now to FIGS. 2 to 4 simultaneously, the internal structure of the tensiometer 20 will be described in more detail. The housing 24 has a peripheral wall 50 which defines a fluid chamber 52 therein. The fluid chamber 52 extends from the first end 26 to the second end 28 of the tubular housing 24. The liquid inlet aperture 36 and the gas inlet aperture 38 extend throughout the peripheral wall 50.

As shown in FIG. 4, the lower portion of the housing 24 is divided in two sections. A seal 54 is inserted between these sections to prevent fluid communication between the fluid chamber 52 and the porous medium 55, in which the tensiometer 20 is inserted.

A pressure transducer 56 is inserted in the fluid chamber 52. The pressure transducer 56 is located above and proximate to the porous tip 30 without being inserted therein. The pressure transducer 56 has a liquid port 58 in fluid communication with the fluid chamber 52. As will be described in more details below, the fluid chamber 52 is designed to be filled with a liquid, typically water, the pressure in the liquid being representative of the matrix water potential sampled through the porous material tip 30.

The pressure of the liquid in the fluid chamber 52, sampled through the liquid port 58, is compared by the pressure transducer 56 to the atmospheric pressure. Therefore, the pressure transducer 56 is in fluid communication with the atmosphere through an atmospheric gas channel 60 which extends longitudinally in the fluid chamber 52. The atmospheric gas channel 60 has a first port 62 connected to a reference port 63 of the pressure transducer 56 and a second port 64 connected to a plug 74 as will be described in more details below.

An electric wire channel 66 also extends longitudinally in the fluid chamber 52. As in the atmospheric gas channel 60, the electric wire channel 66 has a first end 68 connected to the pressure transducer 56 and a second end 70 connected to an electric circuit board 72 located in the head 32 of the tensiometer apparatus 20. The electric wire channel 66 contains electric wires (not shown) in which the data acquired or monitored by the pressure transducer 56 are transferred to the electronic circuit board 72.

The plug 74 (or obstruction member) is inserted in the upper portion of the fluid chamber 52 proximate to the upper end 28 of the tubular housing 24. The plug 74 can be either built in with the housing 24, can be secured to the peripheral wall 50 or can be inserted in the fluid chamber 52 without being mounted to the peripheral wall 50. A fluid channel 76 is defined in the plug 74. The fluid channel 76 has a first section which extends transversally in the plug 74 and a second section which extends longitudinally therein.

The fluid channel 76 has a first port 78, which is in fluid communication with the liquid inlet aperture 36 of the housing 24 when the plug 74 is inserted in the fluid chamber 52, and a second port 80, which is in fluid communication with the fluid chamber 52 and, more particularly, with the section of the fluid chamber 52 extending below the plug 74. The fluid channel 76 is designed to receive a liquid therein to fill the fluid chamber 52, as will be described in more details below.

The peripheral wall defining the transversal section of the fluid channel 76 in the plug 74 can include threads (not shown) for fastening a fluid injector 98 therein, as will be described in more details below.

A gas outlet channel 84 is also defined in the plug 74. The gas outlet channel 84 has a first port 86 in fluid communication, or merging, with the transversal section of the fluid channel 76 proximate to the first port 78. It also has a second port 88 which is in fluid communication with the fluid chamber 52 and, more particularly, with the section of the fluid chamber 52 extending below the plug 74. As will be described in more details below, the gas outlet channel 84 is designed to allow the gas contained in the fluid chamber 52 to exit therethrough while simultaneously filling the fluid chamber 52 with liquid.

Finally, an atmospheric gas channel 90 is also defined in the plug 74. The atmospheric gas channel 90 has a transversal section and a longitudinal section. The atmospheric gas channel 90 has a first port 92 in the transversal section which is in fluid communication with the gas aperture 38 when the plug 74 is inserted in the fluid chamber 52. The atmospheric gas channel 90 has a second port 94 which extends in the fluid chamber 52 and is in fluid communication therewith. As for the ports 80 and 88 of the previously described channels 76 and 84, the second port 94 extends in the section of the fluid chamber 52 which is below the plug 74. The second port 94 is connected to the second port 64 of the atmospheric gas channel 60 and is in fluid communication therewith. The second ports 64, 94 are sealed together to prevent fluid infiltration therebetween.

Referring to FIGS. 2 and 3, it will be seen that the tensiometer 20 can include a fluid injector 98 which can be inserted in the fluid channel 76 for injecting a fluid therein and into the fluid chamber 52 for filling the latter. When inserted in the fluid channel 76, the injector 98 does not obstruct the second port 88 of the gas outlet channel 84 thereby allowing simultaneously gas, previously contained in the fluid chamber 52, to exit therethrough while filling the fluid chamber 52 with liquid.

The injector 98 defines a channel (not shown) in which the liquid circulates. The channel has a first port 102 insertable in the fluid channel 76 through which liquid flows from the channel into the fluid channel 76, and a second port 104 opposed to the first port 102 which is connectable to a fluid supply (not shown). The outer face of the injector 98 can include treads 106 proximate to the first port 102 for connection with the treads defined in the peripheral wall of the fluid channel 76.

In an embodiment, the data acquired by the pressure sensor or pressure transducer 56 are transmitted through electric wires located in the electric wire channel 66 to the electronic circuit board 72 located in the head 32. The data transferred are typically tension data provided in milivolts. These tension data are converted in pressure measures by the electronic circuit board 72. The pressure monitored by the transducer 56 can be displayed on the electronic dial 44 and can also be transmitted to a data logger (not shown) which records the data transmitted from the tensiometer 20. The data can be transferred with wireless technology through the antenna 34 or the tensiometer can be physically connected to a data logger through the connector 42

The other connector 40 is used to connect the tensiometer 20 to a power supply (not shown). The power supply provides power to the tensiometer 20 and, more particularly, to the electric circuitry including the electronic circuit board 72.

To measure matrix water potential in a porous medium, the tensiometer 20 is first inserted in the porous medium. The fluid chamber 52 is filled or refilled with water to ensure that the pressure sensor 56 is immerged. The fluid chamber 52 has, from time to time, to be refilled if the tension, in the porous medium, reaches a critical air breakthrough point. For refilling or filling the tensiometer 20, the injector 98 is inserted in the fluid channel 76 and connected to a fluid supply. A liquid, typically water, is injected into the channel of the injector 98 and flows into the fluid channel 76 to reach the fluid chamber 52.

Simultaneously while the fluid chamber 52 is being filled with liquid, gas previously contained therein exits through the gas outlet channel 84 and the fluid channel 76 which are not obstructed by the insertion of the injector 98. Once the fluid chamber 52 is filled with liquid, the injector 98 is disconnected and removed from the fluid channel 76 and the fluid channel 76 can be closed with a plug (not shown).

Once the tensiometer 20 is connected to a power supply (not shown), the pressure transducer 56, monitors the matrix water potential in the porous medium where the tensiometer 20 is inserted. In accordance with the matrix water potential, liquid is either drawn into or rejected from the porous tip 30 and the pressure in the pores of the porous tip 30 varies accordingly. The pressure in the fluid chamber 52, which is in fluid communication with the porous material tip 30 also varies simultaneously and accordingly. Therefore, the pressure transducer 56, located proximate to the porous tip 30, compares the pressure of the liquid contained in the fluid chamber 52 to the atmospheric pressure. i.e. the transducer 56 measures the pressure caused by the water within the fluid chamber 52 as a function of atmospheric pressure.

The data monitored are transferred to the electronic circuit board 72 which displays, transmits and/or records the data.

The fluid chamber 52 can include a sensor (not shown) to indicate when the fluid chamber 52 needs to be refilled. The tensiometer 20 can send a signal, either through the antenna 34 or through the data logger, connected to the tensiometer 20, to indicate that the tensiometer 20 needs to be refilled. The head 32 can include a GPS or any other positioning system known to one skilled in the art to facilitate the user/farmer to localize the tensiometer 20, which needs to be refilled, in the field. It is also appreciated that the tensiometer 20 can include other warning functions, such as a battery charge level, as described in more details below.

It will be appreciated that the filling/re-filling mechanism can be used with tensiometers 20 having the pressure transducer 56 located externally of the fluid chamber 52 or located higher in the fluid chamber 52. However, it is advantageous to position the transducer 56 proximate to the porous tip 30 since the transducer 56 is kept below the liquid level in the fluid chamber 52 and in fluid contact with both the liquid and the ambient atmosphere. The tensiometer 56 therefore does not require pressure measurement corrections since liquid level variations within the fluid chamber 52 does not affect the monitored pressure measurement. The tensiometer 56 monitors pressure changes relative to atmospheric pressure and is independent of changes in liquid level within the tensiometer 20. Typically, the fluid chamber 52 needs to be refilled when the liquid level is at the level of the upper end of the tensiometer 20.

In the tensiometer 20, the transducer 56 is below the various water levels such that the pressure measurement side of the immersed transducer 56 is open to the water contained with the fluid chamber 52 while the other end of the transducer 56, i.e. the reference port 63, is vented to the atmosphere. An absolute pressure transducer may also be substituted for the transducer described above.

Figure 5:
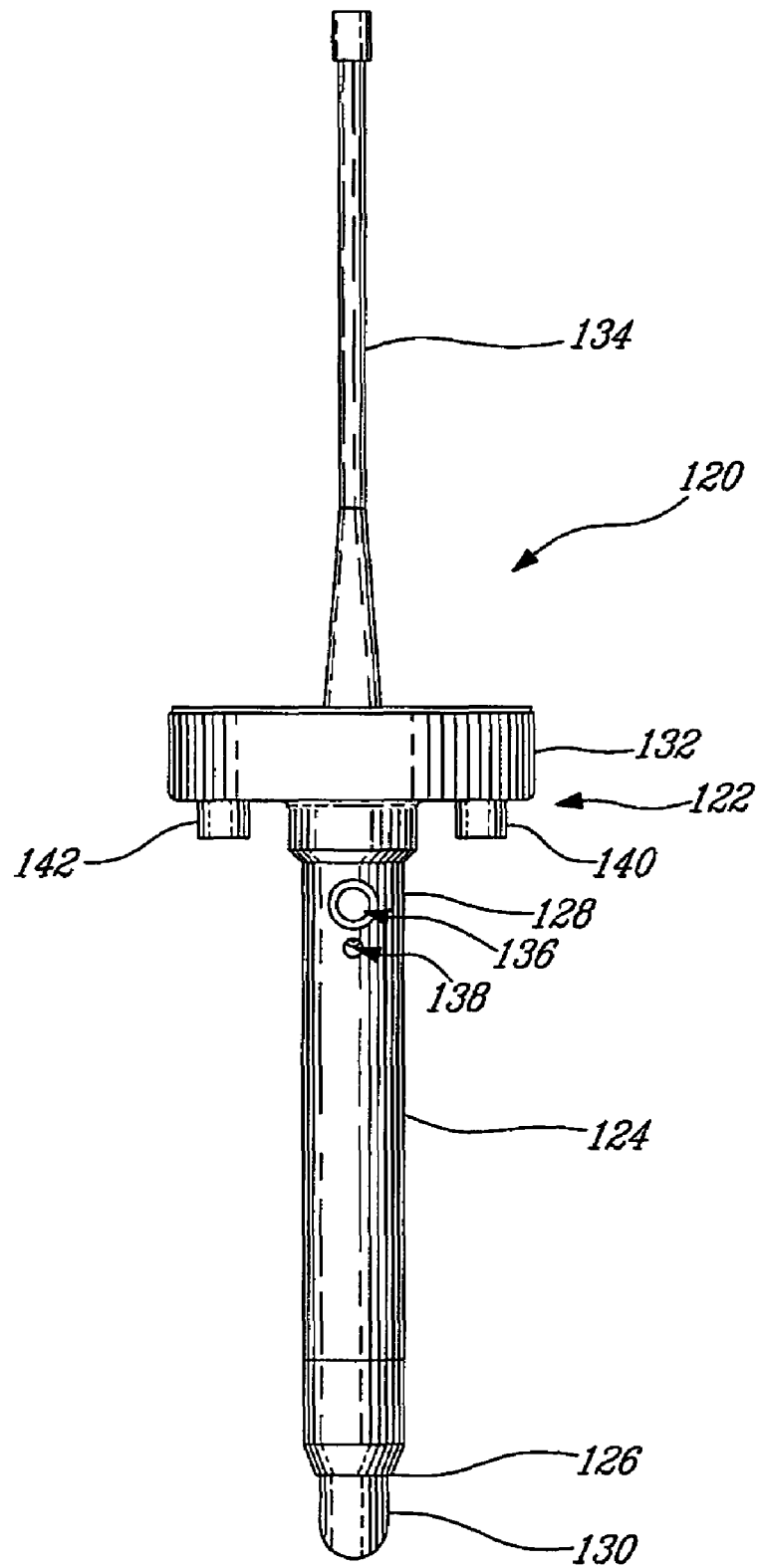
FIG. 5 is a front elevation view of a tensiometer apparatus in accordance with another embodiment of the invention;.
Figure 6:
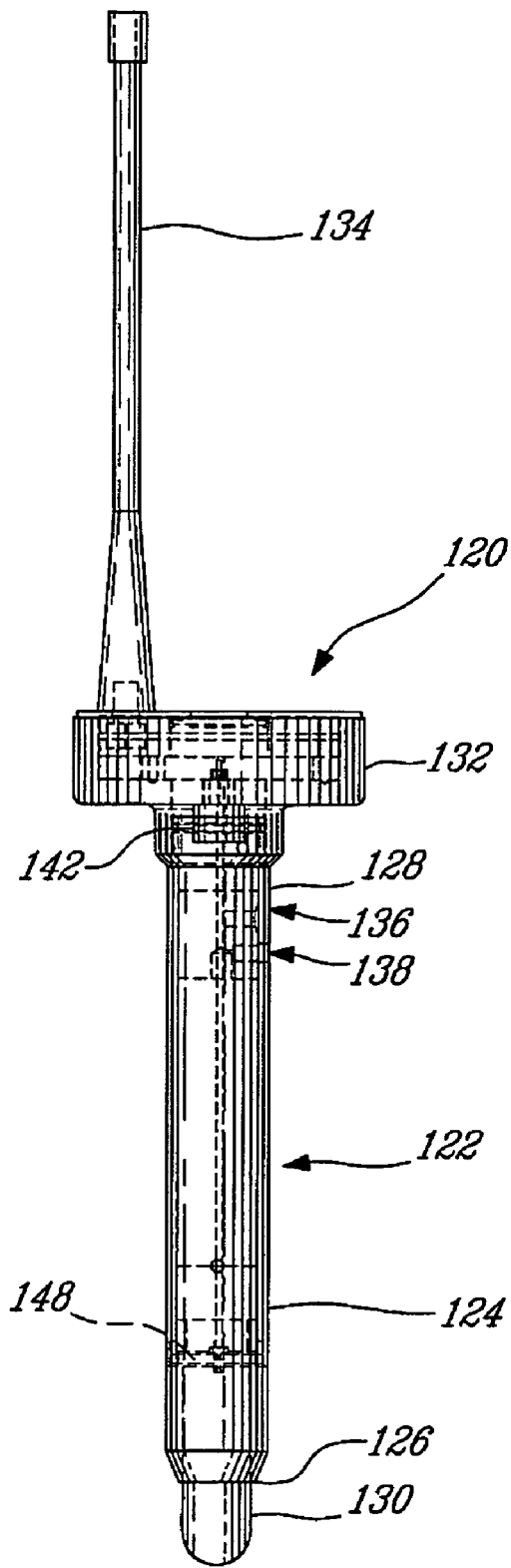
FIG. 6 is side elevation view of the tensiometer apparatus shown in FIG. 5, showing, in dashed lines, internal components of the tensiometer apparatus.
Figure 7:
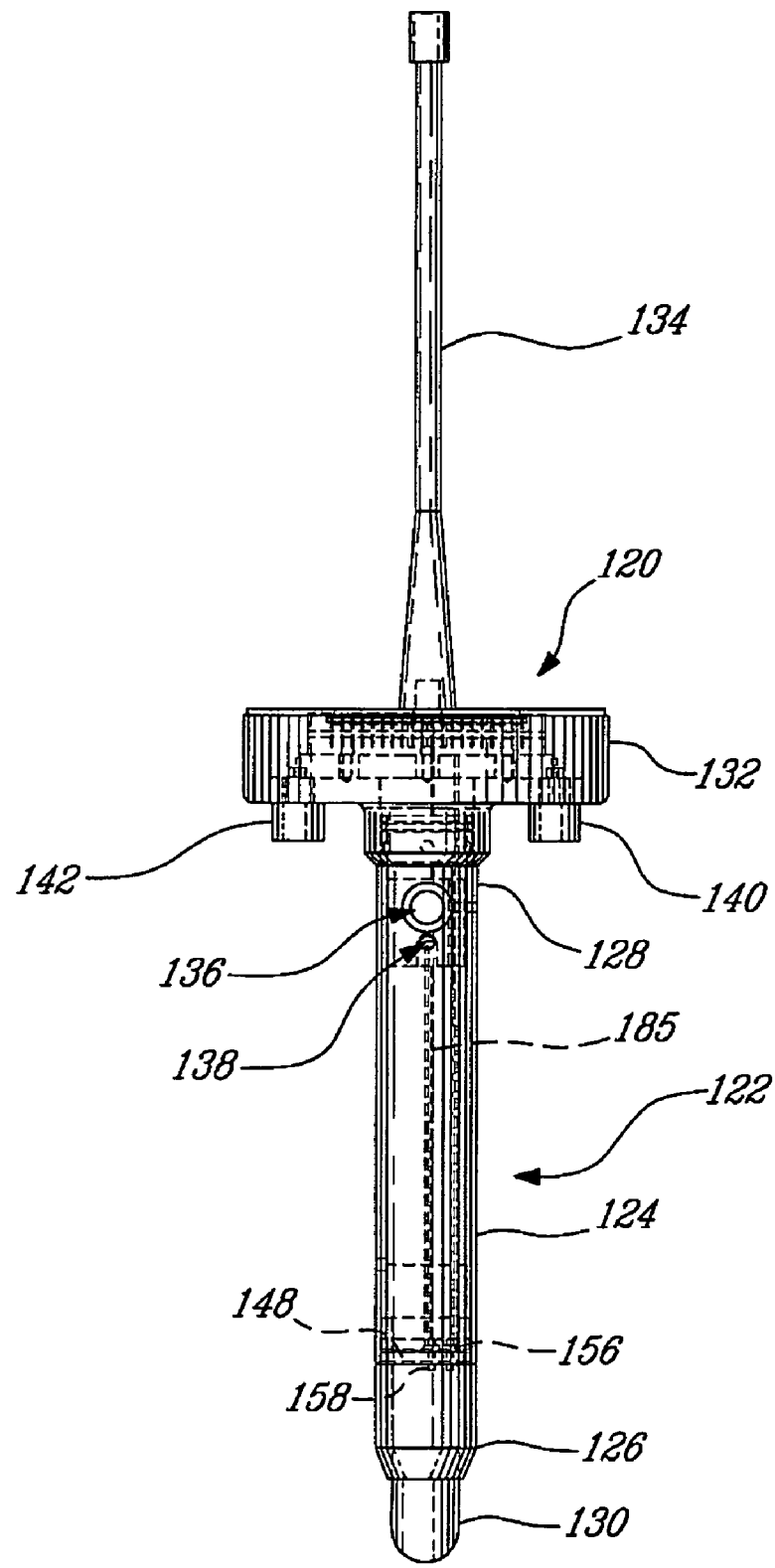
FIG. 7 is front elevation view of the tensiometer apparatus shown in FIG. 5, showing, in dashed lines, internal components of the tensiometer apparatus.
Figure 8:
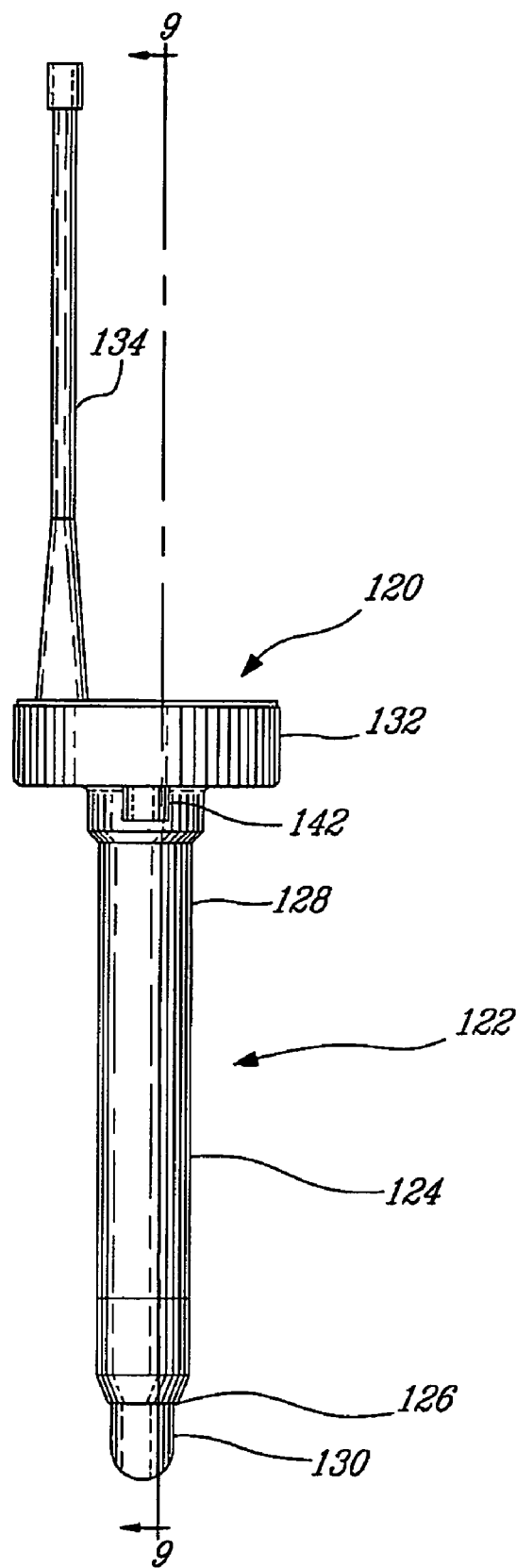
FIG. 8 is side elevation view of the tensiometer apparatus shown in FIG. 5.
Figure 9:
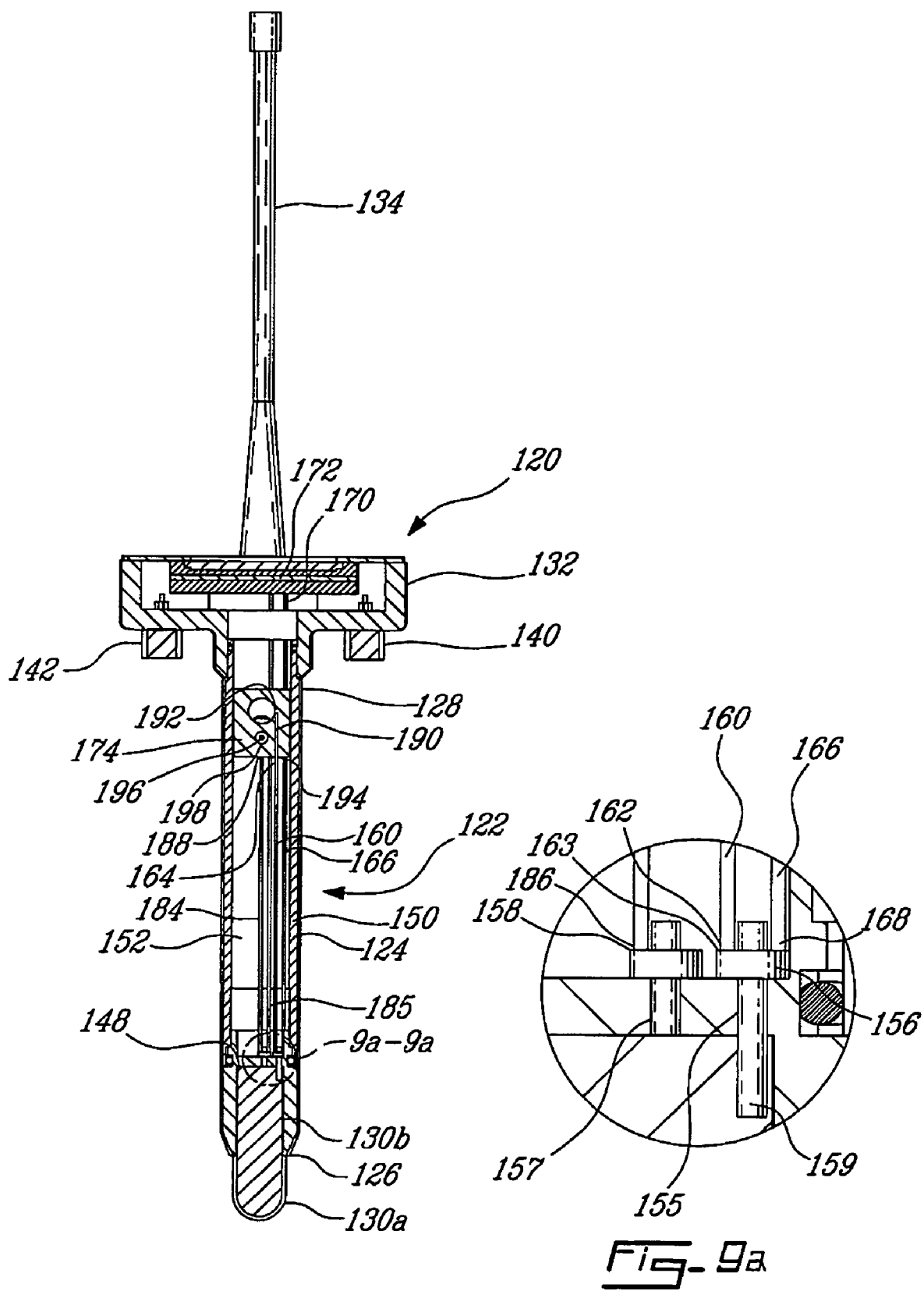
FIG. 9 is a sectional view taken along lines 9-9 of FIG. 8
Figures 10, 10A:
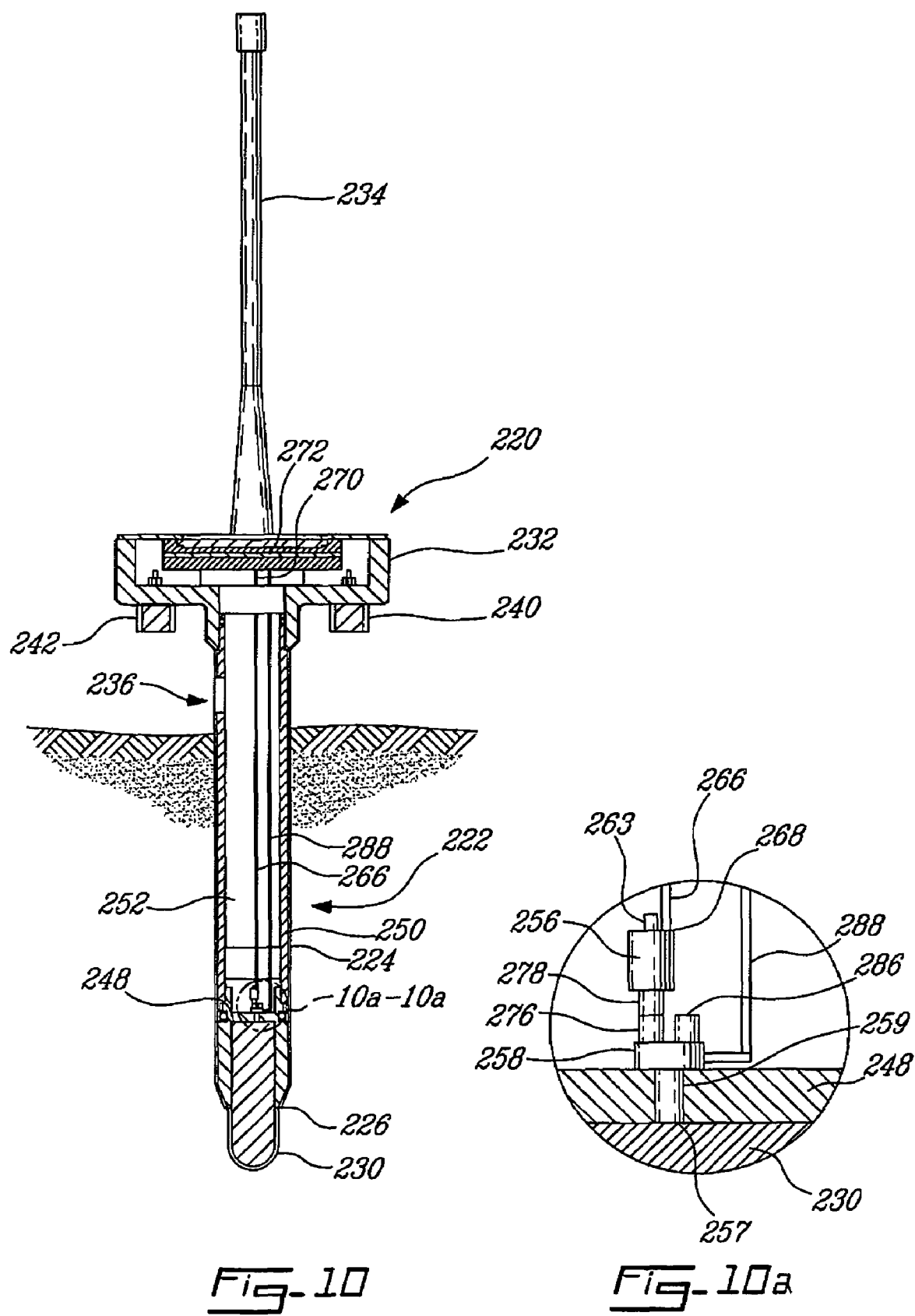
FIG. 10 is a sectional view of a tensiometer apparatus in accordance with another embodiment of the invention, wherein the tensiometer includes pressure transducer in fluid communication with a gas exit valve
FIG. 10a is a detailed view, enlarged, of a section of the tensiometer apparatus shown in FIG. 10.

Referring now to FIGS. 5 to 9, another embodiment of the tensiometer apparatus 20 will be described wherein the features are numbered with reference numerals in the 100 series which correspond with the reference numerals of the previous embodiment. As shown in FIG. 5, the tensiometer 120 is self-priming and is similar to the tensiometer 20. The tubular housing 124 has two apertures extending therethrough, i.e. an atmospheric gas aperture 136 and a gas outlet aperture 138. Contrary to the tensiometer 20, it does not include a liquid inlet aperture 36 since the chamber 152 is not filled with a liquid, as will be described in more details below.

Referring simultaneously to FIGS. 6 to 9, it will be seen the internal components of the tensiometer 120. The porous material tip 130 is mounted to the lower end 126 of the tubular housing 124. The porous material tip 130 can be divided in two sections: a lower section 130a (FIG. 9) in contact with the porous medium when the tensiometer 120 is inserted therein and an upper section 130b (FIG. 9) which is covered by the housing 124. The lower end 126 of the housing 124 is sealed to the outer surface of the porous tip 130 to prevent liquid contained in the porous medium from infiltrating the porous tip 130 therebetween. Therefore, liquid can infiltrate the porous tip 130 through the lower section 130a and flow upwardly into the upper section 130b but cannot infiltrate the porous tip 130 directly through the upper section 130b.

The housing 174 has a peripheral wall 150 which defines a chamber 152. The chamber 152 is isolated from the porous tip 130 with an inner wall 148. Therefore, the chamber 152 is not in fluid communication with the porous tip 130 as in the previously described embodiment. The inner wall 148 has two apertures 155, 157 therein. The first aperture 155 is designed to insert therein a portion of the pressure transducer 156, i.e. an insertion member 159, while the second aperture 157 is designed to insert therein a gas exit valve 158, the purpose of which will be described in more details below.

The insertion member 159 of the pressure transducer 156 extends through the aperture 155 defined in the inner wall 148 and into the porous tip 130. Therefore, the insertion member 159 of the transducer 156 is in fluid communication with the porous tip 130. The upper portion of the transducer 156 extends in the chamber 152.

The pressure of the liquid contained in the pores of the porous material Up 130 and sampled through the insertion member 159 is compared by the pressure transducer 156 to the atmospheric pressure. Therefore, the pressure transducer 156 is in fluid communication with the atmosphere through an atmospheric gas channel 160 which extends in the chamber 152. The atmospheric gas channel 160 has a first port 162 connected to the reference port 163 of the pressure transducer 156 and a second port 164 connected to a plug 174 as will be described in more details below.

An electric wire channel 166 also extends longitudinally in the chamber 152. As in the atmospheric gas channel 160, the electric wire channel 166 has a first end 168 connected to the pressure transducer 156 and a second end 170 connected to an electric circuit board 172 located in the head 132 of the tensiometer apparatus 120. The electric wire channel 166 contains electric wires (not shown) in which the data acquired or monitored by the pressure transducer 156 are transferred to the electronic circuit board 172.

The gas exit valve 158 is in fluid communication with the atmosphere through a gas outlet channel 184 which extends in the chamber 152. The gas outlet channel 184 has a first port 186 connected to the gas exit valve 158 and a second port 188 connected to the plug 174 as will be described in more details below. The gas exit valve 158 is movable between a closed position preventing fluid communication between the porous tip material 130 and the gas outlet channel 184, and an open position allowing gas contained in the pores of the porous material tip 130 to exit therethrough and into the gas outlet channel 184, as will be described in more details below.

A wire 185 extends longitudinally in the chamber 152, between the gas exit valve 158 and the head 132, to provide power to the valve 158.

The plug 174 is inserted in the upper portion of the chamber 152, proximate to the upper end 128 of the tubular housing 124. As for the plug 74, the plug 174 can be either built in with the housing 124, can be secured to the peripheral wall 150 or can be inserted in the chamber 152 without being mounted to the peripheral wall 150.

An atmospheric gas channel 190 is defined in the plug 174. The atmospheric gas channel 190 has a first port 192 which is in fluid communication with the atmospheric gas aperture 136, defined in the peripheral wall 150, when the plug 174 is inserted in the chamber 152. The atmospheric gas channel 190 has a second port 194 which extends in the chamber 152 and is connected to the second port 164 of the atmospheric gas channel 160. These two ports 162, 194 can be sealed together to prevent gas exchanges between the continuous channel defined by the atmospheric gas channels 160,190.

A gas outlet channel 196 is also defined in the plug 174. The gas outlet channel 196 has a first port 198 which is in fluid communication with the gas outlet aperture 138, defined in the peripheral wall 150, when the plug 174 is inserted in the chamber 152. The gas outlet channel 190 has a second port (not shown) which extends in the chamber 152 and is connected to the second port 188 of the gas outlet channel 184. These second ports 188, (not shown) of the gas outlet channel 184 and the gas outlet channel 190 can be sealed together to prevent gas exchanges between the continuous channel defined by the gas outlet channels 184, 196.

As for the previously described embodiment, the data acquired by the pressure sensor or pressure transducer 156 are transmitted through electric wires located in the electric wire channel 166 to the electronic circuit board 172 located in the head 132. The pressure monitored by the transducer 156 is displayed on the electronic dial and/or transmitted to a data logger which records the data transmitted from the tensiometer 120. The data can be transferred with wireless technology with the antenna 134 or the tensiometer 120 can be physically connected to a data logger through the connector 140.

To measure matrix water potential in a porous medium, the tensiometer 120 is first Inserted in the porous medium. The tensiometer 120 is self-priming. Therefore, it does need to be filled or refilled with water to measure matrix water potential.

Once connected to a power supply, the transducer 156 monitors the matrix water potential in the porous medium where the tensiometer 120 is inserted. When inserted in the porous medium, the pores of the porous material tip 130 are filled with gas. Above a threshold value (or critical suction) of matrix water potential, the pores of the porous material tip 130 fill with water, drawn from the porous medium. When the pores draw water from the porous medium, the gas exit valve 158 opens to allow the gas, previously contained therein, to exit therethough and flow outwardly of the tensiometer 120. The threshold value of matrix water potential is characteristic of the properties of the porous material and, more particularly, the pore size. Once the pores filled with water, the gas exit valve 158 closes.

When the matrix water potential in the porous medium increases, the pressure in the pores varies accordingly. Therefore, the transducer 156 compares the pressure in the pores, sampled through the insertion member 159, to the atmospheric gas pressure, provided by the atmospheric gas channels 160, 190 in fluid communication with the atmospheric gas aperture 136.

If the matrix water potential falls below the threshold value, water contained in the pores flows into the porous medium and gas, also provided by the porous medium, fills the pores. Once again, if the matrix water potential of the porous medium rises above the threshold value, the pores re-fill with water, drawing the latter from the porous medium and the valve 158 opens to allow gas exit.

Therefore, when the matrix water potential rises above the threshold value, gas, previously contained in the pores, must escape to be replaced by water. The gas escapes through the gas exit valve 158 which moves between the closed position into the open position. In the open position of the gas exit valve 158, the gas flows upwardly into the valve 158, the gas outlet channels 184, 196, through the gas outlet aperture 138 and into the atmosphere.

Figure 11:
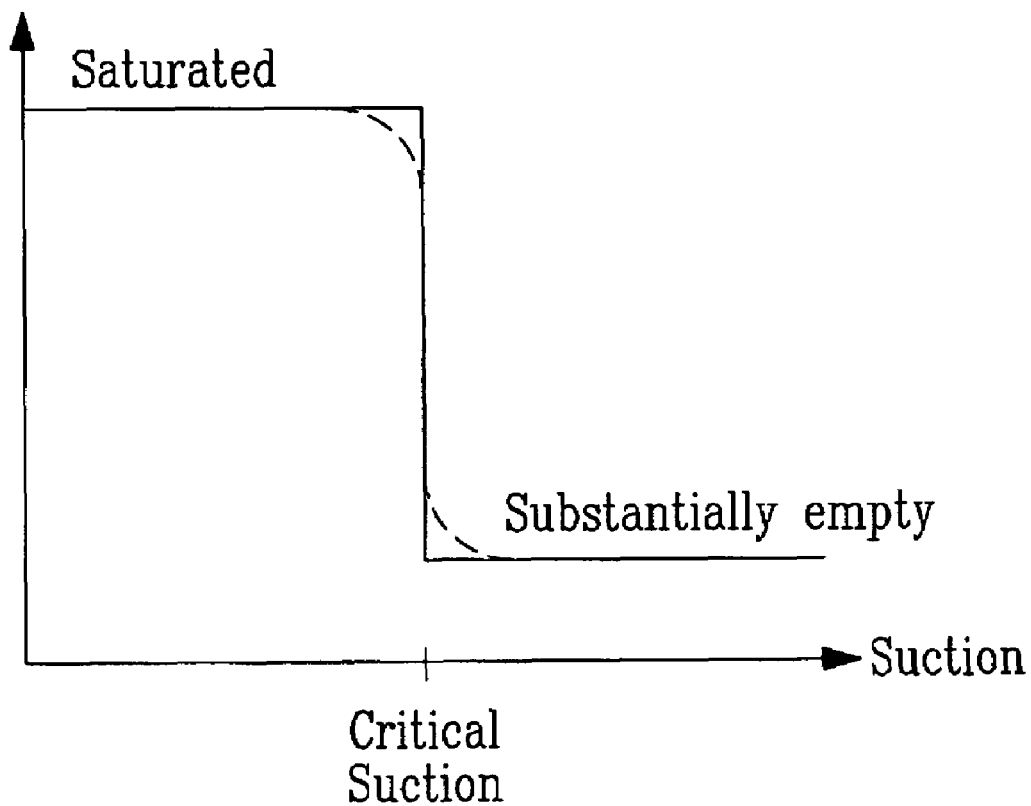
FIG. 11 is a schematic graph showing the quantity of liquid contained in a porous tip of the tensiometer apparatus as a function of the suction measured.

Referring now to FIG. 11, another embodiment of the self-priming tensiometer apparatus 120 will be described wherein the features are numbered with reference numerals in the 200 series which correspond with the reference numerals of the previous embodiment. Instead of having both the gas exit valve 158 and the pressure transducer 156 directly in fluid communication with the porous tip 130, in the tensiometer 220, the pressure transducer 256 is in fluid communication with the porous tip 230 through the gas exit valve 258. Moveover, the chamber 252 does not include a plug 174 inserted therein. The chamber 252 is free of atmospheric gas channel 160 and gas outlet channel 184. The peripheral wall 250 can include an an atmospheric gas aperture 236 extending therethrough and in fluid communication with the chamber 252. Therefore, the gas exit valve 258 is directly in fluid communication with the chamber 252 for releasing gas therein and the reference port 263 of the pressure transducer 256 is directly in fluid communication with the chamber 252 to measure the atmospheric pressure.

The chamber 252 is isolated from the porous tip 230 with the inner wall 248. The inner wall 248 has one apertures 257 therein which is designed to insert therein a portion of the gas exit valve 258, i.e. an insertion member 259.

The insertion member 259 of the gas exit valve 258 extends through the aperture 257 defined in the inner wall 248 up to the porous tip 230. Therefore, the insertion member 259 of the valve 258 is in fluid communication with the porous tip 230. The upper portion of the valve 258 extends in the chamber 252.

The liquid sampled in the pores of the porous material tip 230 flows into the valve 258 towards the transducer 256. The pressure transducer 256 and the gas exit valve 258 are in fluid communication through a liquid port 276 of the valve 258 and a liquid port 258 of the transducer 256.

As for the above described tensiometer 120, the pressure of the liquid contained in the pores of the porous material tip 230 and sampled through the insertion member 259 is compared by the pressure transducer 256 to the atmospheric pressure. Therefore, the pressure transducer 256 is in fluid communication with the atmosphere through the reference port 263. The reference port 263 is in fluid communication with the chamber 252 which is in fluid communication with the atmosphere through the atmospheric gas aperture 236 defined in the peripheral wall 250.

An electric wire channel 266 also extends longitudinally in the chamber 252. The electric wire channel 266 has a first end 268 connected to the pressure transducer 256 and a second end 270 connected to an electric circuit board 272 located in the head 232 of the tensiometer apparatus 220. The electric wire channel 266 contains electric wires (not shown) in which the data acquired or monitored by the pressure transducer 256 are transferred to the electronic circuit board 272.

The gas exit valve 258 is in fluid communication with the atmosphere through a gas outlet port 286 which extends in the chamber 252 and is in fluid communication therewith. As mentioned above, the fluid chamber 252 is in fluid communication with the atmosphere through the atmospheric gas aperture 236 defined in the peripheral wall 250. As for the valve 158, the gas exit valve 258 is movable between a closed position preventing gas contained in the porous tip material 130 to flow into the chamber 252, and an open position allowing gas contained in the pores of the porous material tip 130 to exit therethrough and into the chamber 252. A wire 285 extends longitudinally in the chamber 252, between the gas exit valve 258 and the head 232, to provide power to the valve 258.

As for the previously described embodiments, the data acquired by the pressure sensor or pressure transducer 256 are transmitted through electric wires located in the electric wire channel 266 to the electronic circuit board 272 located in the head 232.

To measure matrix water potential in a porous medium, the tensiometer 220 is first inserted in the porous medium. The tensiometer 220 is self-priming. Therefore, it does need to be filled or refilled with water to measure matrix water potential and its operation is similar to tensiometer 120.

As mentioned above, the critical suction of the porous material tip 130 depends on the characteristics of the porous material constituting the tip 130 and, more particularly, the pore size. Referring to FIG. 11, it will be seen two typical curves representing the suction (or the matrix water potential) as a function of the water contained in the porous material tip 130. The pores are substantially empty above a critical suction, or threshold value. Once the critical value reached, the pores of the porous material tip 130 fills with water until saturation is reached. Even for lower suction value, the water contained in the pores does not increase since water is hardly compressible. In an embodiment, the curve has a step shape (full line), i.e. the pores fill at the critical suction value while, in another embodiment, the pores fill over a threshold suction range surrounding the threshold suction value (dashed line).

Therefore, the pores of the porous material tip 130 auto-fills with liquid when inserted in the porous medium and the porous medium is characterized by a liquid potential at least equal to the threshold suction range (in absolute value). Once the pores filled with liquid, the pressure of the liquid inside the pores is representative of the liquid potential of the porous medium.

It is appreciated that the valve can be replaced by any one-way fluid control device adapted to be in fluid communication with the porous material tip and allowing fluid contained in pores of the porous material and, more particularly, gases to exit therethrough when the porous material tip auto-fills with liquid.

As for the previously described embodiment, the data monitored by the transducer 156 are transferred to the electronic circuit board 172 which displays, transmits and/or records the data.

The tensiometers 20, 120 can be calibrated at the factory, i.e. the readings, in milivolts, obtained from the pressure transducer 56, 156 are automatically converted into cbar or kPa readings by electronics, which prevents the need to run conversion.

Figure 12:
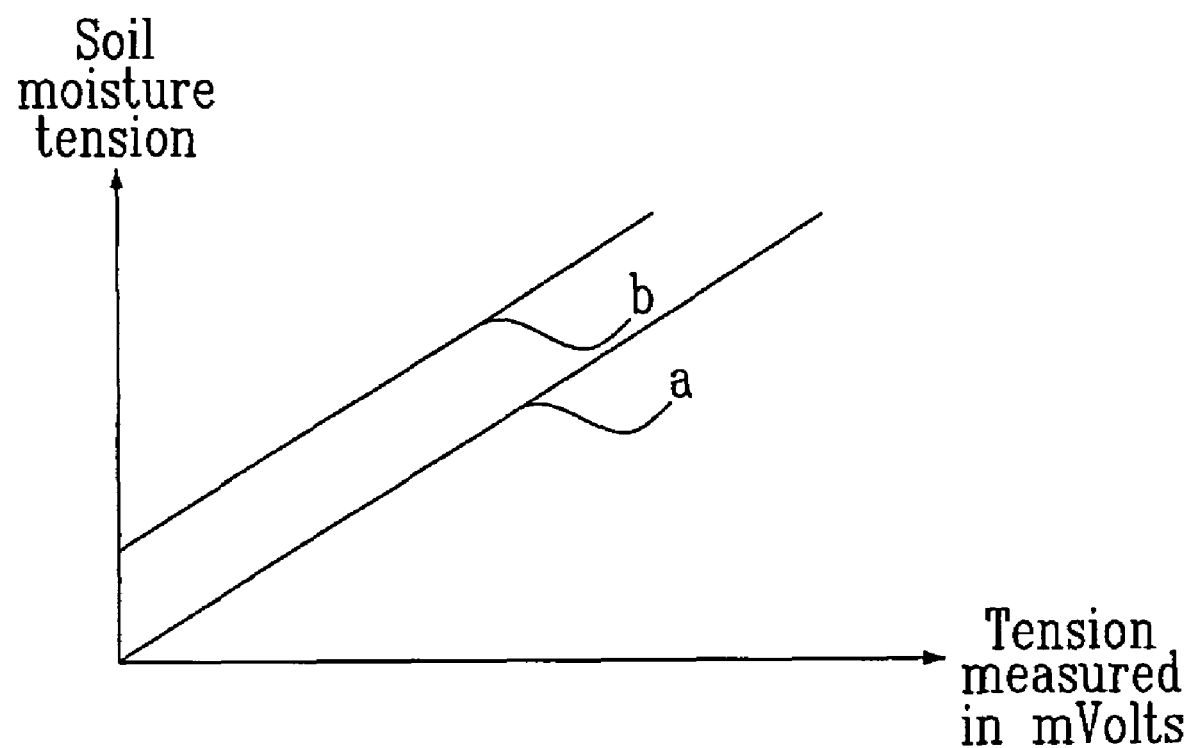
FIG. 12 is a schematic graph showing the soil moisture tension as a function of the pressure measured in millivolts.

As shown in FIG. 12, when the tensiometer 20, 120 drifts (line b), the calibration curve between the milivolt output and the water potential moves parallel to the calibrated curve, upward or downward. To recalibrate the tensiometers 20, 120, the tensiometers 20, 120 are removed from the porous medium and the porous material tip 30, 130 is immersed in water. When immersed in water, the matrix water potential or pressure read by the tensiometer 20, 120 should be void (line a). If the measured value is non-void, the electronic circuit board 72, 172 is recalibrated to obtain a void value.

The porous material tip 30, 130 can have an hollow space, or a depression, therein to obtain faster kinetics, or faster time constant.

The embodiments of the invention described above are intended to be exemplary only.

It will be appreciated that a plurality of tensiometers 20, 120 can be distributed all over the field, the greenhouse or the nursery and are connected to a central station (not shown). For example, the tensiometers can be connected to the central station using radio frequency but they could also be connected by wire or using any other wireless technology such as cell phone technology, satellite telecommunications or an Internet connection using, for example, a cell phone or a device such as a BlackBerry® to connect to the Internet. Each tensiometer 20, 120 can be adapted to repeatedly transmit the sensed data and to also transmit self-check data, such as the battery charge level. The self-check data can be simply Boolean data stating a low battery charge or a low water level. The water level can be not directly monitored but can be inferred from the sensed data received at the central station. When the water tension reaches a given value that is out of the range of the tensiometer 20, the central station determines that the tensiometer 20 needs to be refilled. Alternatively, the water level could be directly read by a sensor and transmitted to the central station. The remote check of the tensiometers 20, 120 is thus provided either using a self-check data transmission, by signal processing of the sensed data at the central station or using a combination of the latter two. Thanks to this feature, the grower is not required to routinely do a round check of the tensiometers 20, 120 in the field but can rely on data received at the central station to plan the maintenance of the tensiometers 20, 120. He will thus only have to go in the field to look for the tensiometers 20, 120 when maintenance is actually required and he will only have to look for the specific tensiometers 20, 120 that requires maintenance.

In order to assist the grower in locating the tensiometers 20, 120 in the field or in the greenhouse, each tensiometers 20, 120 can additionally include a global positioning system (GPS), or any other appropriate positioning system, that provides the position of the tensiometers 20, 120 in real time. The tensiometer coordinates are transmitted to central station where the grower can read the exact position of each tensiometer 20, 120 in the field. In one aspect, it allows him to easily locate the tensiometers 20, 120 to be maintained. In a second aspect, the exact position of each tensiometer 20, 120 is used by the field monitoring software to provide a very accurate map of the soil condition which is very useful in water management and hydrozoning, i.e. providing specific irrigation for each group of plant. Installation of the tensiometer system in the field is also facilitated as the installer does not need to note the position of each tensiometer 20, 120 as it is installed in the field in order to allocate a field zone to each tensiometer 20, 120.

In alternative embodiments, it will be appreciated that the peripheral wall 50, 150 can either be made of a transparent or opaque material. Opaque tubes provide the advantage of having no algae growth within the tensiometer 20.

The transducer 56, or a portion of the transducer 156, reference ports 63, 163, sections of the atmospheric gas channels 60, 160 and the electric wire channel 66, 166, the valve 158, and/or the gas outlet channel 184 can be embedded (or encapsulated) in a substantially solidified material, such as epoxy, (or rigid tubing) to stabilize and protect these components within the tensiometer 20, 120.

The atmospheric gas channels 60, 160, the electric wire channel 66, 166, and the gas outlet channel 184 can be made either of flexible, semi-rigid or rigid tubing.

It will be appreciated that the shape of the tensiometer 20, 120 can vary, that the power supply can be integrated within the tensiometer 20, 120. The fluid chamber 52, and the chamber 152 can be shorter or longer in length than that of the tubular housing 24, 124 respectively. The position of the apertures 36, 38, 136 and 138 in the peripheral wall 50, 150 can be located elsewhere in the tensiometer body 22, 122. The electric wires can extend directly from the pressure transducer 56, 156 to the electronic circuit board 72, 172, i.e. not in the wire channel 66, 166.

It will also be appreciated that the electronic circuit board 72, 172 can be located elsewhere in the housing 24, 124. Several types of pressure transducers 56, 156, which can or cannot compensate for temperature variations, can be used. For example, a piezoresistive pressure transducer can be used. Moreover, it is not necessary for the pressure transducer to be a comparative pressure transducer, i.e. wherein the pressure transducer is in fluid communication with atmospheric gas. In this embodiment, the design of the tensiometer 20, 120 can be modified accordingly.

The electronic circuit board 72, 172 can be replaced by any electronic or mechanical device which can process pressure data.

The plug 74, 174 can be one piece with the housing 24, 124 and/or the head 32, 132. The shape of the fluid channel 76, the gas outlet channel 84, 184 and the atmospheric gas channel 90, 190 can vary from the ones shown in the above-described embodiment.

The first port 86 of the gas outlet channel 84 can merge at a different location with the fluid channel 76 provided that gas can escape without being obstructed when filling the fluid chamber 52 through the fluid channel 76. For example, in an alternative embodiment, the plug 74 cannot include a gas outlet channel 84 which is distinct from the fluid channel 76 to allow simultaneously escape of the gas contained in the fluid chamber 52 while filling the latter with liquid. The diameter of the fluid channel 76 can be larger than the diameter of the injector used to fill the fluid chamber 52 with liquid.

For filling the fluid chamber 52, the tensiometer 20 can be inserted in the porous medium or withdrawn therefrom.

It will also be appreciated that, in the tensiometer 120, the housing 124 cannot include a chamber 152 and the gas outlet channel 184, connected to the valve 158, can communicate directly with the atmosphere.

The scope of the invention is therefore intended to be limited solely by the scope of the appended claims.

The invention claimed is:

1. A porous medium tensiometer comprising:
    a housing defining a fluid chamber therein, having a fluid channel and a gas exit channel extending therethrough, the fluid channel having a first fluid port in fluid communication with the fluid chamber and a second fluid port in fluid communication with the atmosphere, and the gas exit channel having a first gas port in fluid communication with the fluid chamber and a second gas port in fluid communication with the fluid channel, the gas exit channel merging with the fluid channel at the second gas port and being in fluid communication with the atmosphere through the second fluid port, the housing being adapted to be at least partially inserted in a porous medium; and
    a liquid injector insertable in the fluid channel through the second fluid port of the fluid channel for injecting a liquid into the fluid chamber through the first fluid port of the fluid channel and simultaneously ejecting gas contained in the fluid chamber in the atmosphere through the gas exit channel and the second fluid port.

2. A porous medium tensiometer as claimed in claim 1, wherein the housing comprises an inner plug provided above the fluid chamber, the fluid channel extending therein, the housing having a peripheral wall with a fluid aperture defined therein, the fluid aperture being in fluid communication with the second fluid port of the fluid channel.

3. A porous medium tensiometer as claimed in claim 2, wherein the inner plug comprises the gas exit channel with the first gas port in fluid communication with the fluid chamber and the second gas port in fluid communication with the fluid channel; the liquid injector being in fluid communication with the fluid chamber through the first fluid port of the fluid channel and the second gas port of the gas channel being in fluid communication with the fluid aperture of the housing through the fluid channel, when the liquid injector is inserted in the fluid channel.

4. A porous medium tensiometer as claimed in claim 3, wherein the fluid channel is L-shaped with a transversal section, extending in the inner plug from the first fluid port of the fluid channel, followed by a longitudinal section, leading to the second fluid port of the fluid channel, the gas exit channel merging with the fluid channel in the transversal section, at the second gas port of the gas exit channel.

5. A porous medium tensiometer as claimed in claim 4, wherein the liquid injector has a liquid port extending past the second gas port of the gas exit channel when the liquid injector is inserted in the fluid channel.

6. A porous medium tensiometer as claimed in claim 1, comprising a pressure transducer, a circuit board in data communication with the pressure transducer, and a wireless communication network in data communication with the circuit board.

7. A porous medium tensiometer comprising: a housing defining a fluid chamber therein and having an inner plug provided above the fluid chamber, the inner plug having a fluid channel and a gas exit channel extending therethrough, the fluid channel having a first fluid port in fluid communication with the fluid chamber and a second fluid port in fluid communication with the atmosphere, the gas exit channel having a first gas port in fluid communication with the fluid chamber and a second gas port in fluid communication with the fluid channel and merging therewith at the second gas port, the second gas port of the gas exit channel remaining unobstructed when filling the fluid chamber with liquid through the fluid channel and allowing gas contained in the fluid chamber to exit therethrough.

8. A porous medium tensiometer as claimed in claim 7, comprising a liquid injector insertable in the fluid channel through the second fluid port of the fluid channel for injecting a liquid into the fluid chamber through the first fluid port of the fluid channel and simultaneously ejecting gas contained in the fluid chamber in the atmosphere through the second gas and fluid ports of the gas exit channel and the fluid channel.

9. A porous medium tensiometer as claimed in claim 7, wherein the fluid channel is L-shaped with a transversal section, extending in the inner plug from the first fluid port of the fluid channel, followed by a longitudinal section, leading to the second fluid port of the fluid channel, the gas exit channel merging with the fluid channel in the transversal section.

10. A porous medium tensiometer as claimed in claim 9, wherein the liquid injector has a liquid port extending past the second gas port of the gas exit channel when the liquid injector is inserted in the fluid channel.

11. A self-priming tensiometer comprising:
a porous material tip having a first section surrounded by a fluid-impermeable membrane, a second section, a threshold suction range and pores, the pores auto-filling with liquid, through the second section, when in fluid communication with a porous medium having a liquid potential being at least equal, in absolute value, to the threshold suction range, the liquid contained in the pores having a liquid pressure representative of the liquid potential;

a one-way fluid control device in fluid communication with the porous material tip, through the first section, and allowing fluid contained in pores of the porous material to exit therethrough when the porous material tip auto-fills with liquid; and a pressure transducer in liquid communication with the porous material tip and measuring the liquid pressure therein when the pores are filled with liquid.

12. A self-priming tensiometer as claimed in claim 11, wherein the pores of the porous material tip are filled substantially solely by fluid originating from the porous medium when in fluid communication therewith.

13. A self priming tensiometer as claimed in claim 11, comprising a housing having a lower end, an upper end, and an atmospheric gas aperture extending therethrough, the atmospheric gas aperture being in fluid communication with the pressure transducer.

14. A self-priming tensiometer as claimed in claim 13, wherein the porous material tip is mounted to the lower end of the housing and the atmospheric gas aperture and the pressure transducer are in fluid communication through an atmospheric gas channel.

15. A self-priming tensiometer as claimed in claim 13, wherein the one-way fluid control device comprises a one-way valve provided between the porous material tip and the housing, the one-way valve being movable between a closed position preventing fluid communication between the porous material tip and the housing, and an open position allowing gas contained in the pores of the porous material tip to exit through the one-way valve.

16. A self-priming tensiometer as claimed in claim 11, wherein at least one of the pressure transducer and the one-way fluid control device comprises an insertion member inserted in the porous material tip, extending throughout the fluid impermeable membrane, and being in fluid communication with the pores.

17. A self-priming tensiometer insertable in a porous medium, the self-priming tensiometer comprising: a housing; a porous material tip mounted to the housing and having pores and a threshold suction range, the pores being in fluid communication with the porous medium when inserted therein and auto-filing with liquid when the porous medium has a liquid potential at least equal, in absolute value, to the threshold suction range; a pressure transducer in fluid communication with the porous material tip; and a gas exit valve extending between the housing and the porous material tip and movable between a closed position preventing fluid communication between the porous material tip and the housing and an open position allowing gas contained in the pores of the porous material tip to exit therethrough.

18. A self-priming tensiometer as claimed in claim 17, wherein the pores of the porous material tip are filled substantially solely by fluid originating from the porous medium when inserted therein.

19. A self-priming tensiometer as claimed in claim 17, wherein the housing has an atmospheric gas aperture extending therethrough, the atmospheric gas aperture being in fluid communication with the pressure transducer.

20. A self-priming tensiometer as claimed in claim 17, wherein the porous material tip has a substantially uniform pore size.

21. A self-priming tensiometer as claimed in claim 17, wherein the porous material tip has a lower portion in direct contact and in fluid communication with the porous medium when the tensiometer is inserted therein and an upper portion isolated from fluid communication with the housing in the closed position of the gas exit valve.

* * * * *